(12) United States Patent  (10) Patent No.: US 7,526,060 B2
Ziegler                          (45) Date of Patent:  Apr. 28, 2009

(54) ARTIFACT CORRECTION

(75) Inventor: Andy Ziegler, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 189 days.

(21) Appl. No.: 10/598,663

(22) PCT Filed: Mar. 8, 2005

(86) PCT No.: PCT/IB2005/050848

§ 371 (c)(1),
(2), (4) Date: Sep. 7, 2006

(87) PCT Pub. No.: WO2005/088544

PCT Pub. Date: Sep. 22, 2005

(65) Prior Publication Data

US 2007/0276215 A1    Nov. 29, 2007

(30) Foreign Application Priority Data

Mar. 10, 2004  (EP) .................................. 04100966

(51) Int. Cl.
    *A61B 6/00* (2006.01)
(52) U.S. Cl. .......................................................... 378/4
(58) Field of Classification Search .................. 378/4, 378/207, 901
    See application file for complete search history.

(56) References Cited

U.S. PATENT DOCUMENTS

| 4,149,081 | A  | * | 4/1979 | Seppi ............................. 378/5 |
| 5,416,815 | A  |   | 5/1995 | Hsieh |
| 6,507,633 | B1 | * | 1/2003 | Elbakri et al. .................. 378/8 |
| 6,744,848 | B2 | * | 6/2004 | Stanton et al. ................ 378/55 |
| 2002/0154735 | A1 | * | 10/2002 | Simon et al. .................. 378/62 |
| 2003/0128801 | A1 | * | 7/2003 | Eisenberg et al. ............. 378/19 |
| 2003/0156684 | A1 | * | 8/2003 | Fessler ....................... 378/210 |
| 2003/0219152 | A1 | * | 11/2003 | August ....................... 382/131 |
| 2007/0019782 | A1 | * | 1/2007 | Van Stevendaal et al. ...... 378/6 |

FOREIGN PATENT DOCUMENTS

WO    WO 02067201 A1    8/2002

OTHER PUBLICATIONS

Lange et al., Globally Convergent Algorithms for Maximum a Posteriori Transmission Tomography, IEEE Transactions on Image Processing, vol. 4, No. 10, Oct. 1995, pp. 1430-1438.*

Liew et al., Noise Propagation in SPECT images reconstructed using an iterative maximum-likelihood algorithm, Phys Med Biol, 38, 1993, pp. 1713-1726.*

(Continued)

*Primary Examiner*—Edward J Glick
*Assistant Examiner*—Alexander H Taningco

(57) ABSTRACT

The reconstruction of images of an object of interest may introduce artifacts along lines of high gradients of absorption values. According to an exemplary embodiment of the present invention, these artifacts may efficiently be removed by a statistical weighing during reconstruction of the image. Advantageously, according to an aspect of the present invention, the reconstruction of the image may be performed iteratively, wherein the updates are weighted with the intrinsic statistical error of the measured photon counts. This may lead to an efficient removal of artifacts.

18 Claims, 4 Drawing Sheets

OTHER PUBLICATIONS

Wu et al., Tomographic mammography using a limited number of low-dose cone-beam projection images, Med Phys, 30 (3), Mar. 2003, pp. 365-380.*

Knoll et al., Radiation Detection and Measurement, Third Edition, 2000, pp. 65-78.*

Gleason et al., Reconstruction of Multi-Energy Computed Tomography Images of Laboratory Mice, IEEE Transactions on Nuclear Science, vol. 46, No. 4, Aug. 1999, pp. 1081-1086.*

Lang et al., Globally Convergent Alogrithms for a Maximum a Posteriori Transmission Tomography, IEEE Transactions on Nuclear Science, vol. 4, No. 10, Oct. 1995, pp. 1430-1438.*

Erdogan, H., et al.; Ordered subsets algorithms for transmission tomography; 1999; Phys. Med. Biol.; 44:2835-2851.

Lange, K., et al.; Globally Convergent Algorithms for Maximum a Posteriori Transmission Tomography; 1995; IEEE Trans. on Image Processing; 4(10)1430-1450.

* cited by examiner

ARTIFACT CORRECTION

The present invention relates to the field of image processing, for example in medical applications. In particular, the present invention relates to a method of artifact correction in a data set of an object of interest, to data processing devices and to respective computer programs.

In a CT scanner with a polychromatic source of radiation, such as a polychromatic x-ray source, a polychromatic x-ray beam passes through matter and low-energy photons are absorbed as the linear attenuation coefficient generally decreases with energy. As a result, the beam gradually becomes harder, i.e. its mean energy increases. The harder the beam, the less it is further attenuated. Therefore, the total attenuation is no longer a linear function of the thickness of the absorber. This non-linear behavior generally leads to a reduction in the attenuation coefficient. In bone for example, beam-hardening can cause reductions of up to 10%. Neglecting this effect in the reconstruction process leads to well-known beam-hardening artifacts, such as cupping, streaks and flairs.

The reconstruction of CT images can be done with iterative algorithms. These algorithms, in particular iterative maximum-likelihood (ML) reconstruction algorithms, introduce artifacts along lines of high gradients of absorption values. This is well-known from the expectation maximation maximum-likelihood algorithm (EM-ML algorithm). Theses artifacts however are not desired, since they lead to a reduction of image quality.

It is an object of the present invention to provide for an improved image quality.

According to an exemplary embodiment of the present invention, the above object may be solved by a method of artifact correction in a data set of an object of interest, wherein an image of the object of interest is reconstructed on the basis of the data set and wherein a statistical weighing is performed during reconstruction of the image.

Advantageously, this may allow for a correction of artifacts in an image on the basis of a statistical weighing during reconstruction of the image. By weighting weighing certain data in the data set statistically the image quality may be improved significantly.

According to another exemplary embodiment of the present invention, the data set is a projection data set acquired by means of a source of electromagnetic radiation generating a beam and by means of a radiation detector detecting the beam.

Advantageously, this may allow for an artifact correction of CT images acquired in a CT system, which may be used, for example, in the field of medical imaging, and therefore for an improved image quality.

In another exemplary embodiment of the present invention, the source of electromagnetic radiation is a polychromatic x-ray source. Furthermore, according to an aspect of this exemplary embodiment of the present invention, the source moves along a helical path around the object of interest and the beam has one of a cone beam geometry and a fan beam geometry.

The application of polychromatic x-rays may be advantageous, since polychromatic x-rays are easy to generate and provide for a good image resolution. Furthermore, since the geometry of the CT scanner system may be of different designs, such as, for example, cone beam or fan beam geometry, a method of an exemplary embodiment of the present invention may be applied to a plurality of different scanner systems and may not be limited to pure CT scanner systems, but also applicable to positron emission tomography (PET) or single photon emission computed tomography (SPECT).

According to another exemplary embodiment of the present invention, the reconstruction of the image is performed on the basis of an iterative algorithm comprising a plurality of update steps until an end criterion has been fulfilled.

Advantageously, by performing the reconstruction of the image iteratively, mathematical reconstruction methods may be used which comprise transcendental equations which can not be solved exactly. Furthermore, an iterative approach may provide for improved image quality, since the iterative loop may be repeated a plurality of times until the end criterion is met.

According to another exemplary embodiment of the present invention, the iterative algorithm is a maximum-likelihood algorithm and the reconstructed image has the highest likelihood. Furthermore, the weighing is performed in each update step of the plurality of update steps.

Advantageously, a maximum-likelihood algorithm allows for determination of an equation which defines an image with the highest likelihood and a weighing in each update step of the plurality of update steps allows for an efficient compensation or correction of artifacts.

In another exemplary embodiment of the present invention, a number of detected photons during acquisition of the data set is determined and the weighing is based on a statistical error of the number of detected photons.

Thus, the statistical error of the photon counts is estimated and taken into account during the image reconstruction, which may result in an improved image quality with less artifacts.

According to another exemplary embodiment of the present invention, an update of an attenuation parameter $\mu_j^{n+1}$ is calculated from the attenuation parameter $\mu_j^n$ by $$\mu_j^{n+1} = \mu_j^n + \mu_j^n \frac{\sum_i l_{ij} \frac{\sum_i l_{ij}[d_i e^{-<l_i,\mu^n>} - Y_i]/\sigma_{Y_i}^2}{\sum_i l_{ij}/\sigma_{Y_i}^2}}{\sum_i l_{ij} < l_i, \mu^n > d_i e^{-<l_i,\mu^n>}}$$

wherein $d_i$ is a number of photons emitted by the source of radiation, $l_{ij}$ is a basis function of an i-th projection, $l_i$ is a vector of basis functions $l_{ij}$ of the i-the projection and $<l_i,\mu>$ is an inner product, defined by $<l_i,\mu>=\Sigma_j l_{ij}\mu_j$.

This iterative statistical uncertainty weighted algorithm for maximum-likelihood transmission tomography may allow for an effective removal of artifacts by weighing the update with the intrinsic statistical error of the measured photon counts.

According to another exemplary embodiment of the present invention, the reconstruction of the image is based on a sub-set of at least two projections of all acquired projections of the projection data set.

Advantageously, according to this exemplary embodiment of the present invention, performing the statistical weighing on sub-sets of projections may lead to a fast convergence of the image with less artifacts.

According to another exemplary embodiment of the present invention, a data processing device is provided, which comprises a memory for storing a data set and a data processor for performing artifact correction in the data set of the object of interest, wherein the data processor is adapted for performing the following operation: loading the data set and reconstructing an image of the object of interest on the basis of the data set, wherein a weighing is performed during reconstruction of the image and wherein the weighing is based on statistical considerations.

Advantageously, this may allow for an improved image quality of images processed by the data processor which comprise artifacts caused by, for example, high attenuating objects, such as metal.

According to another exemplary embodiment of the present invention, the reconstruction of the image is performed on the basis of an iterative algorithm comprising a plurality of update steps until an end criterion has been fulfilled, wherein the iterative algorithm is a maximum-likelihood algorithm and the reconstructed image has the highest likelihood. Furthermore, the weighing is performed in each update step of the plurality of update steps.

Advantageously, the iterative approach may allow for an improved and fast convergence of the image with less artifacts.

According to another exemplary embodiment of the present invention, a CT scanner system is provided, comprising a memory for storing a data set of an object of interest and a data processor for performing artifact correction in the data set of the object of interest, wherein the data processor is adapted for performing the following operation: loading the data set and reconstructing an image of the object of interest on the basis of the data set, wherein a statistical weighing is performed during reconstruction of the image.

Advantageously, this may allow for an improved CT image quality of for example a part of the body of a patient, wherein the acquired data is processed by the data processor which comprise artifacts caused by, for example, high attenuating objects, such as a prosthesis or other implants.

The present invention relates also to a computer program which may, for example, be executed on a processor, such as an image processor. Such a computer program may be part of, for example, a CT scanner system. The computer program may be preferably loaded into working memories of data processors. The data processors are thus equipped to carry out exemplary embodiments of the methods of the present invention. The computer program may be written in any suitable programming language, for example in C++ and may be stored on a computer readable medium, such as a CD-ROM. Also, these computer programs may be available from a network, such as the WorldWideWeb, from which they may be downloaded into image processing units or processors, or any suitable computers.

It may be seen as the gist of an exemplary embodiment of the present invention that artifacts in an image are corrected on the basis of a statistical weighing during the reconstruction of the image. This may lead to an improved image quality with less artifacts.

These and other aspects of the present invention will become apparent from and elucidated with reference to the embodiments described hereinafter.

Exemplary embodiment of the present invention will be described in the following, with reference to the following drawings.

Figure 1:
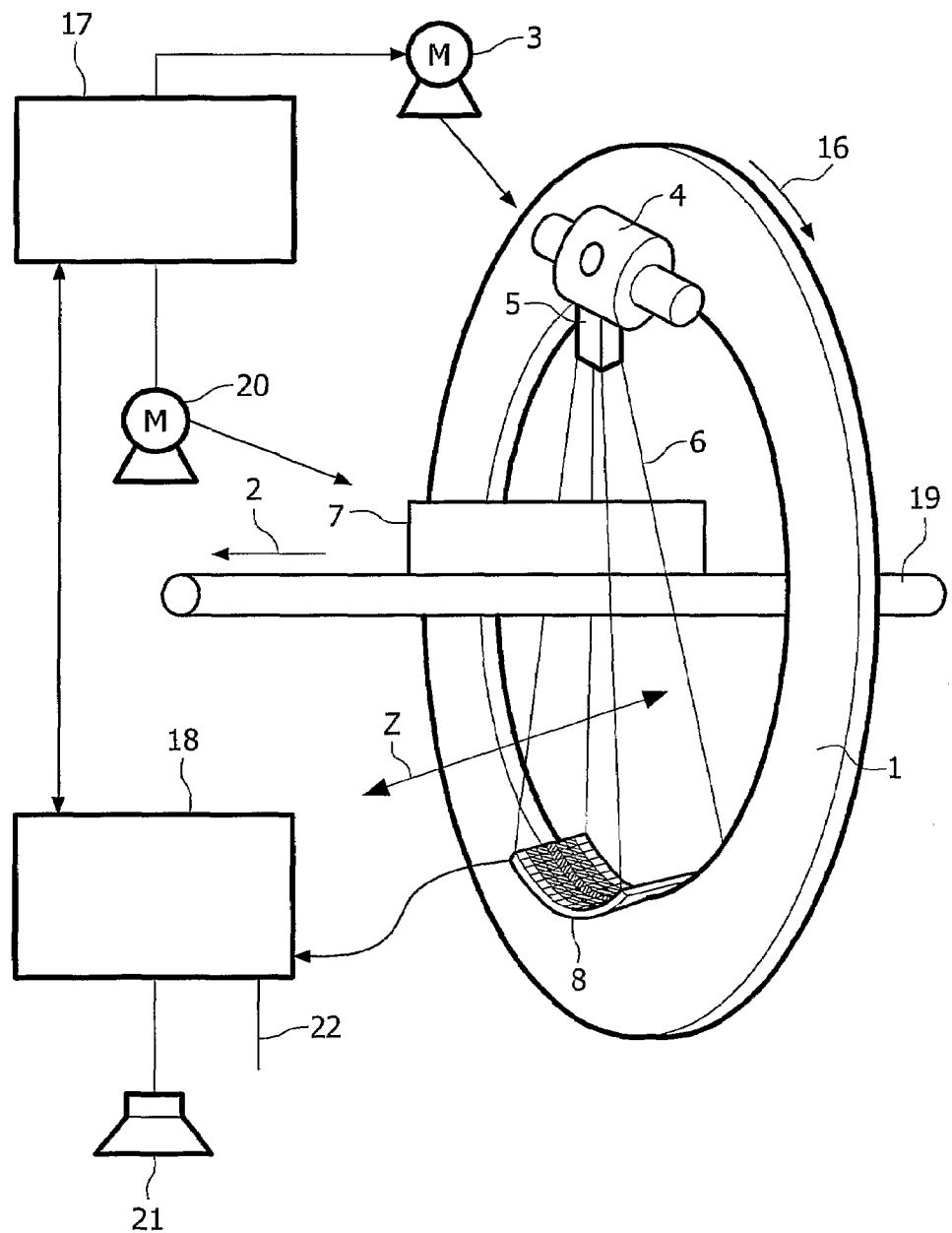
FIG. 1 shows a simplified schematic representation of an embodiment of a computed tomography (CT) scanner according to the present invention.

FIG. 1 shows an exemplary embodiment of a CT (computed tomography) scanner system according to the present invention. With reference to this exemplary embodiment, the present invention will be described for the application in medical imaging. However, it should be noted that the present invention is not limited to the application in the field of medical imaging, but may be used in other applications such as baggage inspection to detect hazardous materials, such as explosives, in items of baggage or other industrial applications such as material testing.

The scanner depicted in FIG. 1 is a cone beam CT scanner. The CT scanner depicted in FIG. 1 comprises a gantry 1, which is rotatable around a rotational axis 2. The gantry is driven by means of a motor 3. Reference numeral 4 designates a source of radiation such as an x-ray source, which, according to an aspect of the present invention, emits a polychromatic radiation.

Reference numeral 5 designates an aperture system which forms the radiation beam emitted from the radiation source to a cone-shaped radiation beam 6. The cone beam 6 is directed such that it penetrates an object of interest 7 arranged in the center of the gantry 1, i.e. in an examination region of the CT scanner, and impinges onto the detector 8. As may be taken from FIG. 1, the detector 8 is arranged on the gantry 1 opposite to the source of radiation 4, such that the surface of the detector 8 is covered by the cone beam 6. The detector 8 depicted in FIG. 1 comprises a plurality of detector elements.

During a scan of the object of interest 7, the source of radiation 4, the aperture system 5 and the detector 8 are rotated along the gantry 1 in the direction indicated by arrow 16. For rotation of the gantry 1 with the source of radiation 4, the aperture system 5 and the detector 8, the motor 3 is connected to a motor control unit 17, which is connected to a calculation unit 18.

In FIG. 1, the object of interest is disposed on a conveyor belt 19. During the scan of the object of interest 7, while the gantry 1 rotates around the item of baggage 7, the conveyor belt 19 displaces the object of interest 7 along a direction parallel to the rotational axis 2 of the gantry 1. By this, the object of interest 7 is scanned along a helical scan path. The conveyor belt 19 may also be stopped during the scans to thereby measure signal slices. Instead of providing a conveyor belt 19, for example in medical applications where the object of interest 7 is a patient, a moveable table is used. However, it should be noted that in all of the described cases it is also possible to perform a circular scan, where there is no displacement in a direction parallel to the rotational axis 2, but only the rotation of the gantry around the rotational axis 2.

The detector 8 is connected to calculation unit 18. The calculation unit 18 receives the detection result, i.e. the read-outs from the detector elements of the detector 8 and determines a scanning result on the basis of these read-outs. The detector elements of the detector 8 may be adapted to measure the attenuation caused to the cone beam 6 by the object of interest 7. Furthermore, the calculation unit 18 communicates with the motor control unit 17 in order to coordinate the movement of the gantry 1 with motor 3 and 20 are with the conveyor belt 19.

The calculation unit 18 may be adapted for reconstructing an image from read-outs of the detector 8. The image generated by the calculation unit 18 may be output to a display (not shown in FIG. 1) via an interface 22.

The calculation unit which may be realized by a data processor may also be adapted to perform an artifact correction in the image based on read-outs from the detector elements of the detector 8. According to an aspect of the present invention, this correction may be performed by reconstructing an image of the object of interest on the basis of the read-outs, wherein a statistical weighing is performed during reconstruction of the image.

Furthermore, the calculation unit for the data processing device may be adapted for performing artifact correction in the data set by performing the reconstruction of the image on the basis of an iterative algorithm comprising a plurality of update steps until an end criterion has been fulfilled, wherein the iterative algorithm is a maximum-likelihood algorithm and wherein the reconstructed image has the highest likelihood. Furthermore, the weighing is performed in each update step of the plurality of update steps.

Furthermore, as may be taken from FIG. 1, for example, the calculation unit 18 may be connected to a loudspeaker 21, for example to automatically output an alarm.

A standard approach for a reconstruction of CT images are iterative algorithms, for example a convex maximum likelihood algorithm. The Maximum Likelihood Method is able to determine an equation which defines an image with the highest likelihood $L(\mu)$ by setting $\partial L(\mu_j)/\partial \mu_j = 0$, where $\mu$ is the vector of attenuation parameters $\mu_j$. Since this equation is transcendental, it cannot be solved exactly, but an iterative approach can lead to the solution. One of these iterative approaches is the "Convex Algorithm" described in K. Lange and J. A. Fessler, "Globally convergent algorithms for maximum a posteriori transmission tomography", IEEE Trans. Med. Imaging 4, 1430-1450 (1995), which is hereby incorporated by reference. The update for one iterative step is found to be $$\mu_j^{n+1} = \mu_j^n + \mu_j^n \frac{\sum_i l_{ij}[d_i e^{-<l_i,\mu^n>} - Y_i]}{\sum_i l_{ij} <l_i,\mu^n> d_i e^{-<l_i,\mu^n>}}, \qquad \text{(equation 1)}$$

where $d_i$ and $Y_i$ are the emitted and observed number of photon counts, respectively, $l_i$ is the vector of basis functions $l_{ij}$ of the ith projection, and $<l_i,\mu>$ is the inner product $\Sigma_i l_{ij}\mu_j$. This update ensures an increasing likelihood in the neighborhood of the optimal point, thus it should lead to an optimal image.

Figure 2:
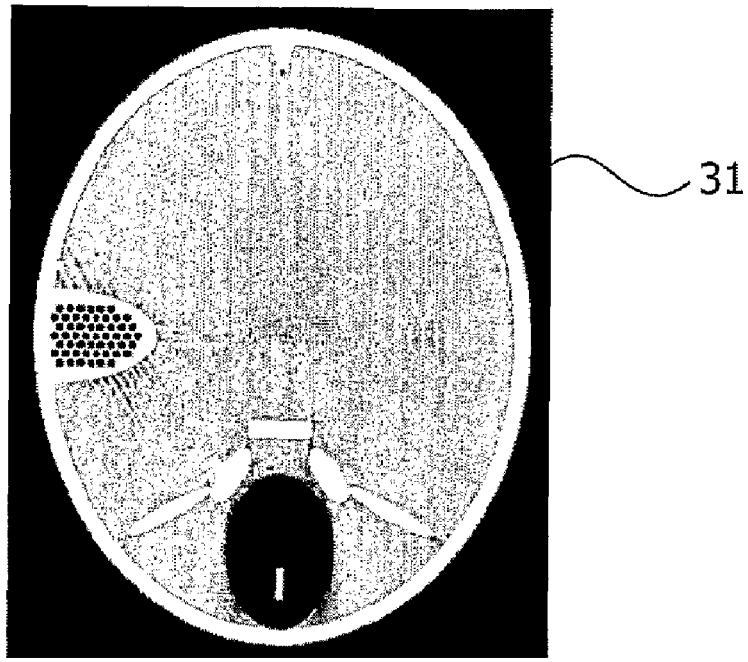
FIG. 2 shows reconstructed image slices of a head phantom using the maximum-likelihood algorithm (left) and the statistical uncertainty weighted maximum-likelihood algorithm according to an exemplary embodiment of the present invention (right).
Figure 2:
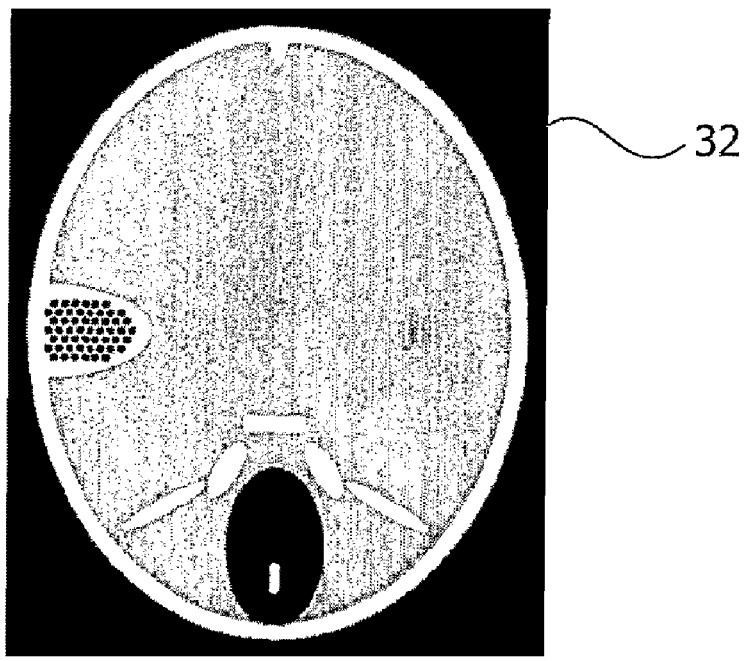

The reconstruction result of such an iterative algorithm is shown as image slice 31 in FIG. 2. Image slice 31 is an image slice of reconstructed projection data of a forbild head phantom. However, as the reconstruction of the head phantom with noise shows, the algorithm according to equation 1 introduces artifacts along lines of high gradients of absorption values. This is well known from the expectation maximum likelihood (EM-ML) algorithm.

The artifacts in the reconstructed image slice 31 occur as streaks. As may be seen from image slice 31 in FIG. 2, without any correction of the artifacts, i.e. without any artifact correction according to an exemplary embodiment of the present invention, a strong streak pattern can be observed.

On the other hand, by reconstructing the image slice according to an exemplary embodiment of the method according to the present invention, in which the subtractions in the updates are weighted with the intrinsic statistical error $\sigma_{Y_i}$ of the measured photon counts $Y_i$ during reconstruction of the image slice, the artifacts are compensated for and the streaks disappear:

$$\mu_j^{n+1} = \mu_j^n + \mu_j^n \frac{\sum_i l_{ij} \frac{\sum_i l_{ij}[d_i e^{-<l_i,\mu^n>} - Y_i]/\sigma_{Y_i}^2}{\sum_i l_{ij}/\sigma_{Y_i}^2}}{\sum_i l_{ij} <l_i,\mu^n> d_i e^{-<l_i,\mu^n>}}, \qquad \text{(equation 2)}$$

where $\sigma_{Y_i} = \sqrt{Y_i}$ is the statistical uncertainty of a Poisson distribution. Each of the updates is hereby the result of a respective cycle of the iterative algorithm.

It should be noted, that the method according to an exemplary embodiment of the present invention also works for a reconstruction with sub-sets of all measured projections.

The image slices shown in FIG. 2 are the result of a convex algorithm (image slice 31), which is a special form of a ML algorithm, and a statistical uncertainty weighted improved convex algorithm (image slice 32), both after 500 iterations and starting from a uniform image. The level is 35 Houndsfield Units (HU), the window is 100 HU.

The convex maximum likelihood algorithm used for reconstructing the image slices of FIG. 2 is described in K. Lange and J. A. Fessler, "Globally convergent algorithms for maximum a posteriori transmission tomography", IEEE Trans. Med. Imaging 4, 1430-1450 (1995), which is hereby incorporated by reference.

Figure 3:
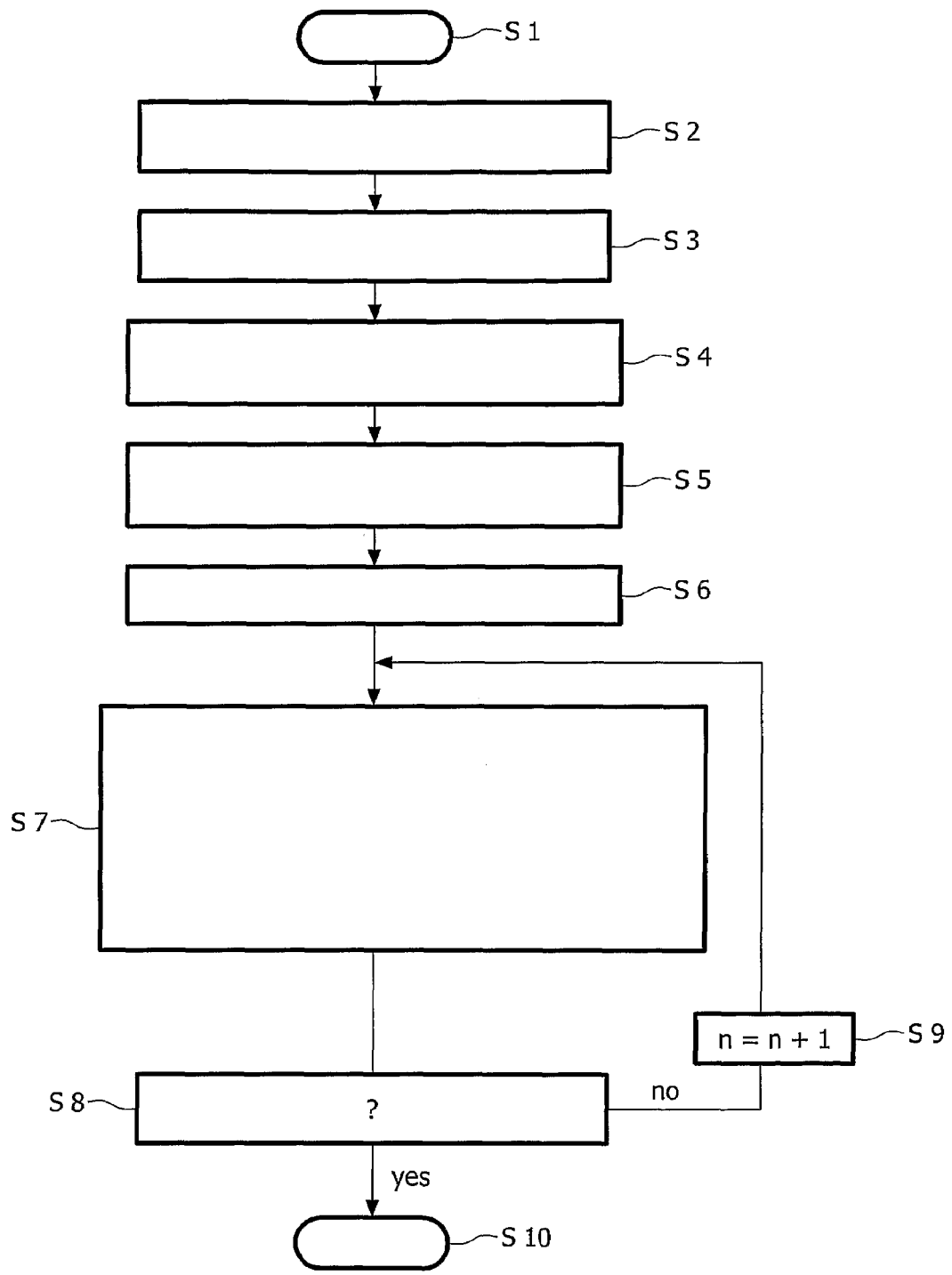
FIG. 3 shows a flow-chart of an exemplary embodiment of a method of artifact correction according to the present invention.

FIG. 3 shows a flow-chart of an exemplary embodiment of a method of artifact correction according to the present invention. After the start in step S1, an acquisition of the projection data set of the object of interest is performed in step S2. This may be performed by detecting a polychromatic x-ray beam emitted from a radiation source, which moves along a helical path around the object of interest. The x-ray beam passes the object of interest and is attenuated by object points inside the object of interest. During the movement of the radiation source a plurality of projections are acquired, each projection belonging to a respective mean position of the radiation source. After acquisition of the projection data set of the object of interest the number of detected photons $Y_i$ of an i-th projection is determined in step S3, e.g. with the help of a data processor. Then, in step S4, the statistical error $\sigma_{Y_i}$ of the number of detected photons $Y_i$ is calculated by the data processor and the vector $\mu$ of attenuation parameters $\mu_j$ is set to an initial value, e.g. $\mu_j=1$, in step S5. Each attenuation parameter $\mu_j$ belongs to a respective interval along the projection line of the i-th projection.

In step S6 then, a counter is set to n=0 after which the iterative loop for the image reconstruction starts. In step S7 the n-th update (which is in case of the beginning of the iterative loop the first update) of the attenuation parameter $\mu_j$ is calculated by $$\mu_j^{n+1} = \mu_j^n + \mu_j^n \frac{\sum_i l_{ij} \frac{\sum_i l_{ij}[d_i e^{-<l_i,\mu^n>} - Y_i]/\sigma_{Y_i}^2}{\sum_i l_{ij}/\sigma_{Y_i}^2}}{\sum_i l_{ij} <l_i,\mu^n> d_i e^{-<l_i,\mu^n>}}$$

Then, the method continues to step S8, where it is determined whether an end criterion is met or not. The end criterion may, for example, be that the iteration has been performed for a certain predetermined number of times or that a difference between consecutive updates does not exceed a certain predetermined threshold value. In case that it is determined in step S8 that the end criterion is not met, the counter is increased by one (step S9) and the method continues with step S7, where (n+1)-th update of the attenuation parameter $\mu_j$ is calculated. Step S7-S9 may be iteratively repeated until the end criterion is met. In case it is determined in step S8, that the end criterion is met, the method continues to step S10, where it ends.

It should be noted that, as may be apparent to the skilled person, the above described technique may be applied to all known reconstruction techniques in which a difference is summarized such as in the convex algorithm described above.

Figure 4:
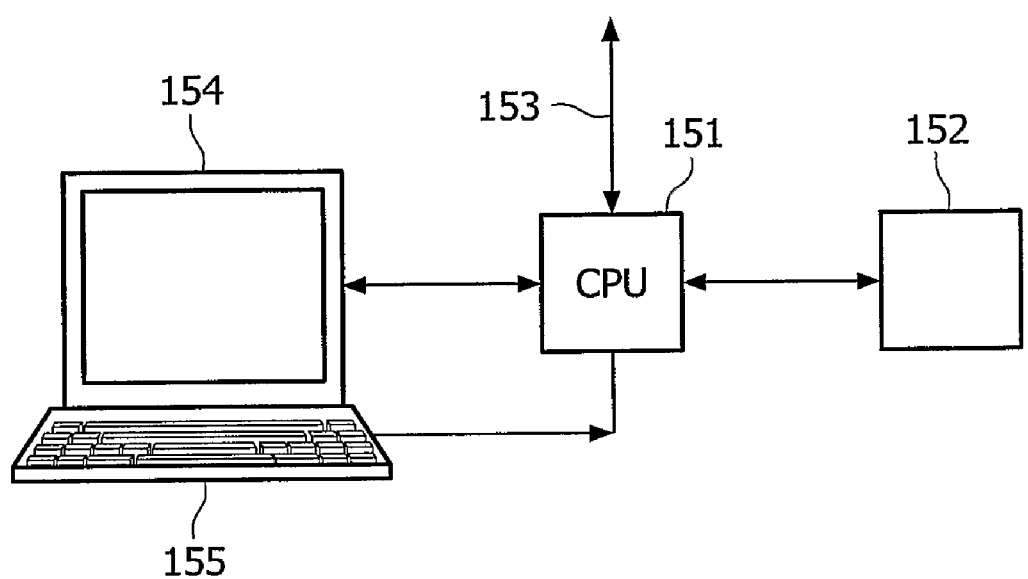
FIG. 4 shows an exemplary embodiment of an image processing device according to the present invention, for executing an exemplary embodiment of a method in accordance with the present invention.

FIG. 4 depicts an exemplary embodiment of a data processing device according to the present invention for executing an exemplary embodiment of a method in accordance with the present invention. The data processing device depicted in FIG. 4 comprises a central processing unit (CPU) or image processor 151 connected to a memory 152 for storing an image depicting an object of interest, such as a patient. The data processor 151 may be connected to a plurality of input/output network or diagnosis devices, such as an MR device or a CT device. The data processor may furthermore be connected to a display device 154, for example a computer monitor, for displaying information or an image computed or adapted in the data processor 151. An operator or user may interact with the data processor 151 via a keyboard 155 and/or other output devices, which are not depicted in FIG. 4.

Furthermore, via the bus system 153, it is also possible to connect the image processing and control processor 151 to, for example a motion monitor, which monitors a motion of the object of interest. In case, for example, a lung of a patient is imaged, the motion sensor may be an exhalation sensor. In case the heart is imaged, the motion sensor may be an electrocardiogram (ECG).

The invention claimed is:

1. A method of artifact correction in a data set of an object of interest, the method comprising the step of: reconstructing an image of the object of interest on the basis of the data set; wherein a statistical weighing is performed during reconstruction of the image, wherein the reconstruction of the image is performed on the basis of an iterative algorithm comprising a plurality of update steps until an end criterion has been fulfilled, wherein each update step comprises subtractions weighted with an intrinsic statistical error $\sigma_Y$, based on measured photon counts $Y_i$, wherein $\sigma_Y$, is the square root of $Y_i$.

2. The method according to claim 1, wherein the data set is a projection data set acquired by means of a source of electromagnetic radiation generating a beam and by means of a radiation detector detecting the beam.

3. The method according to claim 1, wherein the source of electromagnetic radiation is a polychromatic x-ray source; wherein the source moves along a helical path around the object of interest; and wherein the beam has one of a cone beam geometry and a fan beam geometry.

4. The method according to claim 2, further comprising the step of:
   determining a number of detected photons during acquisition of the data set; wherein the weighing is based on a statistical error of the number of detected photons.

5. The method according to claim 2, wherein the reconstruction of the image is based on a sub-set of at least two projections of all acquired projections of the projection data set.

6. The method according to claim 1, wherein the iterative algorithm is a maximum likelihood algorithm; wherein the reconstructed image has the highest likelihood; and wherein the weighing is performed in each update step of the plurality of update steps.

7. The method according to claim 6, further comprising the step of:
   determining a number of detected photons $Y_i$ during acquisition of the data set; wherein the weighing is based on a statistical error $\sigma_{y_i}$ of the number of detected photons $Y_i$; wherein an update of an attenuation parameter $\mu_j^{n+1}$ is calculated from the attenuation parameter $\mu_j^n$ by $$\mu_j^{n+1} = \mu_j^n + \mu_j^n \frac{\sum_i l_{ij} \frac{\sum_i l_{ij}[d_i e^{-<l_i,\mu^n>} - Y_i]/\sigma_{Y_i}^2}{\sum_i l_{ij}/\sigma_{Y_i}^2}}{\sum_i l_{ij} < l_i, \mu^n > d_i e^{-<l_i,\mu^n>}}$$

wherein $d_i$ is a number of photons emitted by the source of radiation;
   wherein $l_{ij}$ is a basis function of an i-th projection;
   wherein $l_i$ is a vector of basis functions $l_{ij}$ of the i-th projection; and
   wherein $<l_i, \mu> = \Sigma_i l_{ij}\mu_j$ is an inner product.

8. The method of claim 1 wherein the end criterion is met only when a difference between consecutive updates does not exceed a threshold value, wherein the threshold value is defined; wherein if the end criterion is not met a counter is increased by one and iterations continue.

9. A data processing device, comprising: a memory for storing a data set of an object of interest; a data processor for performing artifact correction in the data set of the object of interest, wherein the data processor is adapted for performing the following operation: loading the data set; reconstructing an image of the object of interest on the basis of the data set; wherein a statistical weighing is performed during reconstruction of the image; wherein the weighing comprises an intrinsic statistical error $\sigma_Y$, based on measured photon counts $Y_i$, where $\sigma_Y$, is the square root of $Y_i$.

10. The data processing device according to claim 9, wherein the reconstruction of the image is performed on the basis of an iterative algorithm comprising a plurality of update steps until an end criterion has been fulfilled; wherein the iterative algorithm is a maximum likelihood algorithm; wherein the reconstructed image has the highest likelihood; and wherein the weighing is performed in each update step of the plurality of update steps.

11. An apparatus for performing artifact correction in a data set of an object of interest, comprising:
   a processor; and
   a computer readable storage medium encoded with computer executable instructions which, when executed by the processor, causes the processor to perform the following operation loading the data set; and
   reconstructing an image of the object of interest on the basis of the data set; wherein a statistical weighing is performed during reconstruction of the image; wherein the weighing comprises an intrinsic statistical error $\sigma_{Y_i}$, based on measured photon counts $Y_i$, where $\sigma_{Y_i}$ is the square root of $Y_i$.

12. The apparatus of claim 11, wherein the apparatus is connected to a memory for storage of an image depicting an object of interest.

13. The apparatus of claim 11, wherein the apparatus is connected to a plurality of input/output network and diagnostic devices for further analysis and display of stored data and information.

14. the apparatus of claim 11, wherein the apparatus is further connected to a motion monitor which may monitor the physiological capacities of an object of interest.

15. The apparatus according to claim 11, wherein the processor also determines a number of detected photons during acquisition of the data set.

16. the apparatus of claim 11, wherein the processor further sets a set of attenuation parameters $\mu_j$ to an initial value, wherein each attenuation parameter $\mu_j$ belongs to a respective interval along a projection of an i-th projection.

17. The apparatus of claim 11, wherein the processor further calculates the attenuation parameters $\mu_j$ by:

$$\mu_j^{n+1} = \mu_j^n + \mu_j^n \frac{\sum_i l_{ij} \frac{\sum_i l_{ij}[d_i e^{-<l_i,\mu^n>} - Y_i]/\sigma_{Y_i}^2}{\sum_i l_{ij}/\sigma_{Y_i}^2}}{\sum_i l_{ij} <l_i,\mu^n> d_i e^{-<l_i,\mu^n>}}$$

wherein $d_i$ is a number of photons emitted by the source of radiation; wherein $l_{ij}$ is a basis function of an i-th projection; wherein $l_i$ is a vector of basis functions $l_{ij}$ of the i-th projection;

and wherein $<l_i, \mu> = \Sigma_j l_{ij}\mu_j$ is an inner product.

18. The apparatus according to claim 11, wherein the reconstruction of the image is based on a sub-set of at least two projections of all acquired projections of the projection data set.

* * * * *